United States Patent [19]

Orlowski et al.

[11] 4,220,582

[45] Sep. 2, 1980

[54] DENTAL RESTORATIVE COMPOSITIONS OF IMPROVED X-RAY OPACITY

[75] Inventors: Jan A. Orlowski, Altadena; Patrick D. Kidd, Sierra Madre; David V. Butler, West Covina, all of Calif.

[73] Assignee: Lee Pharmaceuticals, South El Monte, Calif.

[21] Appl. No.: 667

[22] Filed: Jan. 3, 1979

Related U.S. Application Data

[63] Continuation of Ser. No. 804,291, Jun. 7, 1977, abandoned.

[51] Int. Cl.² .......................... C08K 3/22; C08K 3/36; C08K 3/40
[52] U.S. Cl. .............................. 260/42.28; 260/42.29; 260/42.37; 260/42.52; 260/998.11; 433/228
[58] Field of Search ............. 260/42.28, 42.52, 998.11, 260/42.29, 42.37

[56] References Cited

U.S. PATENT DOCUMENTS

| | | | |
|---|---|---|---|
| 3,751,399 | 8/1973 | Lee et al. | 260/42.28 |
| 3,769,336 | 10/1973 | Lee et al. | 260/42.28 |
| 3,808,170 | 4/1974 | Rogers | 260/37 ED |
| 3,826,778 | 7/1974 | Dietz | 260/42.52 |
| 3,959,212 | 5/1976 | Rockett | 260/42.53 |
| 4,017,454 | 4/1977 | Muller | 260/42.52 |
| 4,028,325 | 6/1977 | King | 260/42.52 |
| 4,029,632 | 6/1977 | Gross et al. | 260/998.11 |

OTHER PUBLICATIONS (I) Bowen, R. L., X-R-Opaque Reinforcing Fillers for Composite Materials, J. Dent. Res., 48, pp. 79–82 (1969).

(II) Bowen, R. L., A New Series of X-Ray-Opaque Reinforcing Fillers forComposite Materials, J. Dent. Res., 51,177 (1972).

*Primary Examiner*—James H. Derrington
*Attorney, Agent, or Firm*—Irons & Sears

[57] ABSTRACT

Dental restorative compositions of improved X-ray opacity are described. These compositions comprise from 30% to 85% by weight of the composition of a finely divided inorganic filler and from 15% to 70% by weight of the composition of a liquid resin binder. The filler comprises at least 60% by weight of the filler of a ground barium glass that has a barium oxide (BaO) content greater than about 22.5% by weight of the glass. By appropriate selection of the binder, the composition may cure in a single stage of curing, or it may set in two stages, to provide a period of time during which it can be carved to a desired shape.

4 Claims, No Drawings

DENTAL RESTORATIVE COMPOSITIONS OF IMPROVED X-RAY OPACITY

This is a continuation of application Ser. No. 804,291, filed June 7, 1977, now abandoned.

FIELD OF THE INVENTION

This invention relates to dental restorative compositions of superior opacity to dental diagnostic X-rays. More particularly, the invention relates to dental restorative compositions that contain finely divided filler and liquid resin binder that can be activated to cause setting within a few minutes, wherein the filler imparts improved opacity to dental diagnostic X-rays.

STATE OF THE ART

The first direct dental filling compositions using acrylate binders that were not only accepted by the dental profession, but that were commercially successful, were based on the use of mixtures of bisphenol A backbone monomers and reactive diluent acrylic monomers, as described by H. L. Lee, Jr., et al. in U.S. Pat. No. 3,539,533. Dr Lee has remained an active contributor to the art, and was one of the inventors in the following U.S. patents, among others, that relate to dental restorative compositions: U.S. Pat. Nos. 3,730,947; 3,769,336; and 3,770,811.

The presence in a direct dental filling composition having an acrylate binder of a very substantial amount of an inorganic filler usually imparts some degree of X-ray opacity to fillings and restorations formed from these materials. It has long been recognized that opacity to X-rays can be imparted to such filler materials by the incorporation of an element of relatively high atomic weight. The successful production of radioopaque filler materials has not been without its problems, however.

Glasses having relatively high contents of barium oxide have been suggested for use as fillers. Such glasses exhibit a high absorption of short wave length X-ray radiation, which is the kind ordinarily used in dental diagnosis. When such glasses are used in fillers, the X-ray absorption is such that it is possible to distinguish the filling made from the composition from the tooth structure and also from caries and underlying decalcified dentin.

There have been suggestions in the art for the use of lithium aluminum silicates containing a rare earth element such as, for example, lanathanum, since the rare earth elements generally have a high molecular weight and impart X-ray opacity. However, the use of alkaline elements in silicate glasses is generally recognized as not desirable because of their affinity for water and tendency to migrate. Rightly or wrongly, they are suspected of creating conditions that are favorable for a form of stress corrosion that might increase the rate of surface material loss.

The use of barium-containing glasses has been somewhat restricted, in the past, because when a filler contains less than about 10% by weight of barium oxide based on the filler weight, X-ray opacity is either marginal or not adequate. When the filler contains above about 50 parts by weight of a barium aluminum silicate glass, based on the total weight of the filler, and that glass has a barium content measured as barium oxide greater than about 22.5% by weight, difficulty has been experienced in matching the refractive index of the filler with that of the resin binder.

SUMMARY OF THE PRESENT INVENTION

The present invention is a dental restorative composition comprising a finely divided filler admixed with a liquid resin binder, that cures to form a hard dental restorative material of enhanced opacity to dental diagnostic X-rays.

A dental restorative composition in accordance with this invention comprises from 30% to 85% and preferably 65% to 85% by weight of the composition of a filler, and from 15% to 70% and preferably 15% to 35% by weight of the composition of a liquid resin binder. The filler comprises at least 60% by weight thereof of a ground barium glass having a content of barium oxide greater than about 22.5% by weight thereof.

According to preferred embodiments of the invention, particular liquid resin binders are employed that make it possible to use fillers having such a high level of barium glass content while at the same time, clearly superior properties are exhibited, particularly with respect to opacity to dental X-rays.

Depending upon the particular liquid resin binder that is selected, and the manner in which it cures, the composition may be one that cures within about 2 minutes after mixing, or it may be one that goes through two curing steps, to provide a phase in which the filling has the consistency of soap, so that it can be carved to a desired shape.

Dental restorative compositions prepared in accordance with the present invention may be packaged in conventional fashion, in two or more packages, each of which is individually shelf stable, but which, upon mixing, form a composition that cures within about 10 minutes at most. Such compositions may be used in a variety of restorative applications, and particularly for direct dental filling applications.

For use of these compositions, a cavity, fissure, or a broken tooth surface is prepared, and a composition in accordance with the present invention is applied while it remains flowable, so that it can conform to the contours of the tooth surface against which it engages. The composition is applied in such a way as to insure complete and full contact, and then is shaped roughly. The composition sets rapidly once it is in place, hardening in situ. It is polished after it reaches the requisite hardness.

DESCRIPTION OF PREFERRED EMBODIMENTS OF THE INVENTION

The present invention has several features that combine, particularly in preferred embodiments of the invention, to provide dental restorative compositions of superior characteristics.

One of the important features of the invention is the use of a filler that contains at least 60% by weight of barium glass that in turn has a barium content, measured as barium oxide, of at least 22.5% by weight of the barium glass. It would be expected that a dental restorative composition having a filler containing more than about 50% by weight of a barium silicate glass would be inferior from the point of view of aesthetics because of the difficulty of matching the refractive index of the liquid resin binder with that of the filler. However, the particular resin binders employed in connection with the present invention produce attractive restorations despite the higher barium glass content of the filler, and thus produce restorations of clearly superior opacity to dental diagnostic X-rays.

The introduction of barium oxide into a glass formulation raises its refractive index. The commercially avilable glasses, that contain a desirable amount of barium for use in fillers of dental restoratives, have refractive indexes that are rather high for the intended application. The proper selection of liquid resin binders is one way in which the high refractive index is accommodated. Moreover, many commercially available barium glasses contain alkali elements, such as sodium, potassium, or lithium. These elements can catalyze the hydrolysis of silica and have other possibly deleterious effects when present in the dental cavity. Accordingly, barium glasses are used in the practice of the present invention, that are free from monovalent elements.

The barium glass that is selected for use should be transparent and should have a low coefficient of thermal expansion. Since barium-containing glasses tend to have higher thermal expansions than many of the commonly used filler materials for dental restorative compositions, such as fused silica, one preferred filler composition consists of 60% by weight of the filler of a barium glass, as more particularly defined hereafter, together with 40% by weight of amorphous silica.

The filler ordinarily constitutes from about 30% to about 85% by weight of a dental restorative composition made in accordance with the present invention. The amount of filler selected will depend upon the problems of installation, and the kind of restorative work that is required. For direct dental filling applications, it is generally desirable to have a rather high content of filler, to reduce shrinkage, enhance compressive strength, and for other reasons that are well known. Consequently, for direct dental filling formulations, a filler content in the range from about 70% by weight to about 85% by weight of the overall composition represents a preferred range. For other applications, such as, for example, the preparation of caps, or for other such applications where an initially low viscosity may be important to permit some flow to conform to a desired mold shape, a lower amount of filler may be desirable. This invention is, however, primarily concerned with direct dental filling applications.

The filler itself should include at least 60% by weight of a barium glass, finely ground, that contains at least 22.5% by weight of barium measured as barium oxide, and that is essentially free of monovalent elements. Suitable barium glasses are barium oxide-based boron-alumina-silicate glasses, generally made from mixtures of silica, boron oxide, alumina, and barium oxide. Generally, the amount of barium, expressed as barium oxide, that should be present in such a barium glass, for present purposes, is above 22.5% by weight of the glass, and preferably above 30% by weight of the glass. Stated in another way, the amount of barium in the barium glass, measured as barium oxide, should be above about 13 mol % or 14 mol % of the glass. When a filler is used in a direct dental filling composition in accordance with the present invention, the barium, measured as barium oxide, should contribute, preferably, at least about 13% to 14% by weight of the total composition, and preferably, at least about 15% by weight of the total composition. Generally, the barium oxide present will not contribute more than about 26% to 28% by weight of the total composition.

Usually the barium glass contributes at least 60% by weight of the filler, but it may constitute 100% by weight of the filler. Intermediate amounts between 60% and 100% by weight of the filler can, of course, be used.

A preferred second material, for use in conjunction with a barium glass, is amorphous silica. Other materials that could be employed include fused silica, crystalline quartz, mixtures of these, and other inorganic particulate materials selected to contribute desired properties to the final composition.

Several commercially available barium glasses can be used for the practice of the present invention. One such suitable commercially available glass is disclosed in U.S. Pat. Nos. 3,801,344 and 3,975,203. These patents disclose barium aluminosilicate glasses that generally contain from about 22.5% to 72%, and preferably 50% to 60% of barium measured as barium oxide, from none to about 42%, and preferably from about 10% to about 20% of alumina ($Al_2O_3$), and from about 15% to about 58%, and preferably from 25% to 35% of silica, all percentages being by weight based on the glass. Suitable barium aluminosilicate glasses should be essentially free from monovalent elements such as lithium, sodium, and potassium. Glasses of this kind are available from Owens-Illinois, Inc.

Another suitable, preferred glass is available from Corning Glass Works, Inc., as Corning Glass 7724. This is a barium silicate glass that contains an amount of barium oxide that is present in a substantially equimolar percentage to the sum of the molar percentages of the alumina and boron oxide present. A representative composition has a nominal barium oxide content of 32% by weight, together with about 50% by weight of silica, and with almost equal weight percentages of alumina and boron oxide ($B_2O_3$).

Still another satisfactory barium glass is available under the trademark Raysorb T-2000 from Kimble, a division of Owens-Illinois. This glass has a thermal expansion of 6.7 ppm per °C., a refractive index of 1.59, and a barium oxide content of 46%.

The filler is utilized in finely divided form, having a particle size generally in the range from about 1 micron to about 30 microns. Preferred fillers will have generally the characteristics specified in U.S. Pat. No. 3,792,531, of Carl J. Rossi. Preferably, the filler will have been pretreated in accordance with the procedure described in copending application Ser. No. 401,808, of Lee and Orlowski, filed Sept. 28, 1973. The disclosures of that patent, and of the pending patent application, are incorporated herein by reference.

Best results are obtained if the filler particles are treated with a keying agent to improve the bond between the liquid resin binder and the surfaces of the finely divided filler particles. Keying agents that have been found to be highly suitable are the ethylenically unsaturated organo-silane finishing or keying agents. One preferred keying agent is alpha-methacrylpropyl trihydroxy silane. The finely divided filler may be treated with the keying agent in the manner described in the copending U.S. patent application Ser. No. 662,226, of Lee, Stoffey and Orlowski, filed Feb. 27, 1976, which is a continuation of Ser. No. 436,680, filed Jan. 25, 1974, now abandoned, which in turn was a continuation of Ser. No. 146,465, filed May 24, 1971, now abandoned, all of which are incorporated herein by reference.

THE LIQUID RESIN BINDER

For Direct Dental Filling Compositions With a Single Step Cure

When used herein as a generic term (rather than as a part of the name of a specific chemical compound), the terms "acrylate" and "diacrylate" are intended to mean both acrylate and methacrylate, and diacrylate and dimethacrylate, respectively.

The liquid resin binder, for use in accordance with the present invention, is a diacrylate or a dimethacrylate, that can cross-link upon curing. One convenient form of binder is made from either bisphenol-A-bis-(3-methacryloyl-2-hydroxy propyl) ether (bis-GMA) or from the dimethacrylate of ethoxylated bisphenol-A (EBA), or from a mixture of these, together with a cross-linking diacrylate or dimethacrylate such as, for example, a di-, tri-, or polyethylene glycol dimethacrylate.

Another suitable material for use as at least a part of the liquid resin binder is (methacryloyl ethyl)-(methacryloyl-2-hydroxypropyl) hexahydro phthalate. Other similar dimethacrylates can also be used.

Such other preferred binder materials, that cross-link upon polymerization, are provided by a diacrylate or dimethacrylate of an alicyclic dicarboxylic acid selected from the group consisting of hexahydrophthalic acid, tetrahydrophthalic acid, and a maleic acid adduct of methylcyclopentadiene. More specifically, such binder materials comprise a diacrylate of the formula:

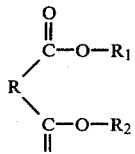

Where:

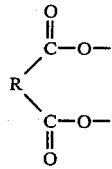

is the residual moiety of an organic alicyclic dicarboxylic acid selected from the group consisting of hexahydrophthalic acid, tetrahydrophthalic acid, and a maleic acid adduct of methylcyclopentadiene, and wherein $R_1$ and $R_2$ are the residual moieties of the same or different hydroxyalkyl or epoxyalkyl esters of acrylic acid or methacrylic acid, respectively. The adduct of methylcyclopentadiene with maleic acid or its anhydride is available commercially as "Nadic Methyl Anhydride", hereinafter "NMA." The term "Nadic" is a trademark of Allied Chemical Corporation.

While this group of these three kinds of alicyclic o-dicarboxylic acids have been found to be eminently suitable for present purposes, other such acids may also be used such as, for example, some of the substituted hydrogenated phthalic acids such as the lower alkyl-substituted tetrahydro and hexahydrophthalic acids.

These last-named binder materials permit ease of manufacture. When made in a stepwise reaction, the production process, which involves exothermic reactions, is easily controlled, and the more precise control that is possible permits the production of binders with preselected, more uniform viscosities and refractive indices than is feasible otherwise.

To form the desired diacrylate adduct, a two-step process is employed, in which the material that furnishes the acid component is reacted first with one material to form an acrylate monoester, and then with a second material, to form the diacrylate adduct.

While the material that serves as the source of the acid is not necessarily the acid or its anhydride, as is well understood by those in this art, the anhydride is a convenient and inexpensive acid source. Thus, hexahydrophthalic anhydride is reacted with a hydroxyalkyl acrylate or methacrylate to produce a monoester, which is then reacted with an epoxyalkyl acrylate or methacrylate to produce the diester adduct. In place of the hexahydrophthalic anhydride, the anhydrides of tetrahydrophthalic acid or of NMA may be used. Similarly, in place of the hydroxyethylmethacrylate, other hydroxyalkyl esters of acrylic and methacrylic acids may be used. Similarly, in place of the glycidyl methacrylate, other epoxyalkyl esters of acrylic and methacrylic acid may be substituted.

The resultant adducts may be used in combination with other resin materials in a paste composition, such as, for example, ethylene glycol dimethacrylate, diethylene glycol dimethacrylate, triethylene glycol dimethacrylate, other polyglycol dimethacrylates, Bis-GMA, and like monomers that are acceptable for use in the dental composition field. The polyglycol dimethacrylates are particularly useful because, generally, they have low viscosity and low surface tension, and they thus improve workability prior to cure.

To make the adduct of tetrahydrophthalic acid (THPA) with hydroxyethyl methacrylate (HEMA) and glycidyl methacrylate (GMA), a mixture was made in a reactor of 2,006 gms. HEMA (2.5% excess), 2,280 gms. THPA, 8 gms. BHT, and 16.5 gms. triphenyl phosphine catalyst. The mixture was heated to 85° C. to 90° C. with constant stirring, in an atmosphere of dry air. After several hours of reaction in a constantly renewed atmosphere of dry air, the reaction was determined to be about 58% complete. At this point, glycidyl methacrylate (GMA) additions were commenced, in a stepwise fashion.

As the first step, 423.5 gms. of GMA were added. The temperature rose to 105° C. within 15 minutes, then fell to 90° C.–95° C. After 1½ hours, an additional 422.5 gms. GMA were added. The temperature rose about 10° C. within 15 minutes, then dropped back to 90° C. After two hours, no free GMA was present, and an additional 498.5 gms. of GMA were added, with a rise in temperature of 4° C.–5° C. After 1 hour, 407 gms. more GMA were added, with no perceptible temperature rise. After 1 hour, the final 379 gms. of GMA was introduced, again with no noticeable change. The total amount of GMA added was thus 2,130 gms.

The reaction mix was heated for a total of 24 hours at 85° C.–90° C., after which the residual GMA was 4%–6%. The product, (methacryloyl ethyl)-(methacryloyl-2-hydroxypropyl) tetrahydro phthalate, was removed from heat, and the yield was about 100% of the crude adduct product. The epoxy equivalent was 74,633, and the refractive index $n_D^{22}$ was 1.4891, as compared to the theoretical value 1.4850.

Other similar adducts can be prepared in the same fashion. Thus, the adduct of hexahydrophthalic anhydride with hydroxyethyl methacrylate and glycidyl methacrylate can be made in the same stepwise fashion. Such an adduct is characterized by improved color stability upon exposure to sunlight or other source of ultraviolet radiation. A typical index of refraction for such a product is 1.4865 at 23° C.

Direct Dental Filling Compositions With Two Step Cure

Restorative compositions that are designed to permit the dentist to shape them by carving cure in two steps. During the initial step, the composition cures to a hardness sufficient to permit carving. At this stage of cure, the composition will have a Shore D hardness of about 45, and a consistency like that of a bar of soap. Generally this is intended to occur after about 3 minutes or so after mixing. By about 6 minutes after mixing, the composition ordinarily will have cured sufficiently to have attained a Shore hardness of about 85, after which it cannot easily be carved. After about 8 to 10 minutes, sufficient hardness has been attained to permit finishing.

Carvable dental restorative compositions are described in the copending application of Henry L. Lee, Jr. and Jan A. Orlowski, Ser. No. 669,174, filed Mar. 22, 1976, which is incorporated herein by reference. The liquid resin binder for such compositions includes polymerizable substances that have at least two polymerizable groups, having different reactivity rates under the conditions of polymerization employed. Exemplary monomers that contain at least two groups of different reactivity include: allyl methacrylate, allyl acrylate, allyl glycidyl ether, diallyl fumarate, diallyl maleate, glycidyl methacrylate, butene-1,4-dimethacrylate, butene-1,4-diacrylate, 4-hydroxy butene methacrylate, 4-hydroxy butene acrylate, and 1-methacryloyl-2-acryloyl-propane. Other suitable compounds will be readily apparent to the skilled artisan. With these monomers, it is possible to form compositions using only the single monomer or to use the monomer in admixture with other monomers such as the mono or diacrylates or methacrylates, for example, 2,2-bis[4'(-3"-methacryloyl-2"-hydroxy propoxy) phenyl]propane (known as Bis-GMA), polyethylene glycol dimethacrylate, cyclohexyl methacrylate, and mixtures thereof.

Instead of employing a bifunctional monomer or prepolymer, it is, as aforementioned, possible to employ two monomers containing functional groups of different reactivity. These monomers may, for example, be selected from the following compounds: diglycidyl ether of bisphenol A, diallyl phthalate, mono-, di or polyethylene or polypropylene glycol dimethacrylate, dimethacrylates such as, for example, 1-(2'-methacryloylethoxy)-2-(3'-methacryloyl-2'-hydroxy propoxy) cyclohexane, methyl methacrylate, Bis-/GMA, 2-hydroxyethyl methacrylate, 2-hydroxypropyl methacrylate, glycidyl methacrylate, 2-hydroxyethyl acrylate, ethyl methacrylate, ethyl acrylate, cyclohexyl methacrylate, cyclohexyl acrylate, diallyl methacrylate, diallyl acrylate, 2-aminoethyl methacrylate, 2-aminoethyl acrylate, ethylene glycol diacrylate, diethylene glycol diacrylate, triethylene glycol diacrylate, tetraethylene glycol diacrylate, styrene, and triallyl cyanurate.

Suitable polymerizable substances may contain at least two polymerizable groups selected from vinyl, allyl, acryl, methacryl and styryl groups such that the composition upon polymerization would reach a Shore D hardness of about 85 at least about two minutes, and preferably about four minutes, after the composition reaches a Shore D hardness of 45 in order to afford the dentist adequate time for hand carving of the composition. Desirably, reactive groups and conditions will be selected so that the composition will reach the gel state within about two minutes after initiation of the polymerization, and a Shore D hardness of about 45 within about four minutes after initiation of the polymerization.

OTHER COMPONENTS

Dental restorative compositions of the kind contemplated in accordance with the present invention are normally supplied to the dentist in two separate packages. Each package contains a paste. One of these pastes contains a catalyst, and is generally referred to as the catalyst paste. The other paste contains an activator for the catalyst, and it is generally referred to as the neutral paste. To use the material, a dentist mixes the two pastes, generally in equal amounts, to form a curable dental restorative composition. Since the curable composition is designed to cure and harden within ten minutes at most, generally, it must be used promptly.

Catalysts are usually employed in amounts from about 0.2% to about 5% by weight of the liquid resin binder. Generally, amounts of from about 0.25% to about 2.5% by weight of the liquid resin binder are satisfactory. Peroxide catalysts are preferred, generally in amounts in the range from about 1% to about 2% by weight based on the weight of the liquid resin binder. Benzoyl peroxide is preferred, but other catalysts well known in the art may be employed.

The amount of accelerator used depends upon the particular resin compositions that are utilized and the working time that is desired. Generally accelerators can be employed in amounts of 0.001% by weight of the monomeric materials utilized. Usually about 0.5% to 1% of an activator by weight of the binder system is sufficient. Examples of suitable accelerators are N,N-dimethyl-para-toluidine, para-toluene sulfinic acid, N-bis (hydroxy-ethyl)-p-toluidine, para-tolyl diethanolamine, and other tertiary amines which are well known in the art.

Minor amounts of a polymerization inhibitor and/or antioxidant may be included. Thus, in order to inhibit unwanted polymerization during extended shelf storage, it is permissible to include 60-110 ppm. hydroquinone. An example of an antioxidant employed is 2-tert-butyl-4-methyl-phenol in an amount of from 0.05% to 1.0% based on the total weight of monomer present in the binder system.

The invention is further exemplified below by several specific demonstrations thereof in accordance with preferred embodiments of the invention. In the following examples, and throughout this application, all parts and percentages are by weight unless otherwise specified, and all temperatures are reported in degrees Celsius unless otherwise specified.

EXAMPLE 1

Direct Dental Filling Composition

A direct dental filling composition was made up in the form of two pastes.

The neutral paste was made up from the following components:

| Neutral Paste Liquid Resin Binder | |
|---|---|
| Ingredient | Parts by Weight |
| Bisphenol-A-bis-(3-methacryloyl-2-hydroxypropyl)ether(Bis-GMA) | 60.0 |
| Dimethacrylate of ethoxylated bisphenol A (EBA) | 20.0 |

| -continued | |
|---|---|
| Triethylene glycol dimethacrylate | 20.0 |
| Butylated hydroxy toluene (inhibitor) (BHT) | 0.06 |
| UV-9 (UV absorber) (2-hydroxy-4-methoxybenzophenone) | 1.5 |
| N,N-bis(2-hydroxyethyl)-p-toluidine (Accelerator A) | 2.8 |
| Aerosil fumed colloidal silica (modifier) | 1.0 |

| Filler | |
|---|---|
| Ingredient | Parts by Weight |
| Radiopaque glass G | 60.0 |
| Amorphous silica | 40.0 |

The filler particles were treated with a solution of a silane primer in methylene chloride, to have a silane content of 3.5% by weight deposited thereon after drying.

As an initial step in preparing a filling composition for use, the binder and filler were mixed together to form a paste, in the ratio of 4.1 parts of filler to 1.0 parts of binder, by weight.

The catalyst paste was made up from the following components:

| Catalyst Paste Liquid Resin Binder | |
|---|---|
| Ingredient | Parts by Weight |
| (methacryloylethyl)(methacryloyl-2-hydroxypropyl) hexahydro phthalate | 100.0 |
| BHT (inhibitor) | 0.12 |
| UV-9 (UV absorber) | 0.60 |
| Aerosil fumed colloidal silica (modifier) | 1.0 |

| Filler | |
|---|---|
| Ingredient | Parts by Weight |
| Radiopaque glass G | 60.0 |
| Amorphous silica | 40.0 |

The filler particles were treated with a silane keying agent to have a silane content of 3.5% by weight, and were admixed with 0.42 parts by weight of benzoyl peroxide as a catalyst.

The resin binder and filler were mixed to form the catalyst paste, in the ratio of 4.0 parts of filler to 1.0 parts of binder, by weight.

Radiopaque glass G had a refractive index of 1.545. It was in the form of fine particles, of which 95% pass through a 325 mesh screen, and 99% through a 200 mesh screen (U.S. Standard Sieve). A sieve analysis indicated the following particle size distribution:

| % | Smaller than (in micrometers) |
|---|---|
| 50 | 5 |
| 89 | 20 |
| 80 | 13.5 |
| 20 | 1.7 |
| 9 | 1.0 |

The particle size range was essentially from about 0.6 micrometers to about 50 micrometers.

The approximate chemical composition of this glass was:

| | Wt. % | Mol % |
|---|---|---|
| $SiO_2$ | 51 | 67 |
| $B_2O_3$ | 8.7 | 9.6 |
| $Al_2O_3$ | 8.3 | 6.4 |
| BaO | 32 | 16.9 |

Density as measured by the water displacement method is approximately 2.9 g/cc. Thermal expansion is about 5.26 ppm per °C.

Trace elements present (as impurities) include:

| | |
|---|---|
| PbO | 0.01% |
| CuO | 0.01% |
| $As_2O_3$ | 0.002% |
| $Sb_2O_3$ | 0.001% |
| $Fe_2O_3$ | 0.100% |

Direct Dental Filling Composition

The two pastes were mixed in equal parts, to form a filling composition ready to use in a previously prepared cavity. The compressive strength, measured after 24 hours, was 43,280 psi, which is considered to be a very good value. The $C_{70}$ value and X-ray opacity were evaluated as better than existing formulae.

EXAMPLE 2

Direct Dental Filling Composition 100% Radiopaque Filler

Another direct dental filling composition was made up in the form of two pastes.

| Neutral Paste Liquid Resin Binder | |
|---|---|
| Ingredient | Parts by Weight |
| Bis-GMA | 60.0 |
| EBA | 20.0 |
| Triethylene glycol dimethacrylate | 20.0 |
| BHT (inhibitor) | 0.06 |
| UV-9 (UV absorber) | 1.5 |
| Accelerator A | 2.8 |
| Aerosil fumed colloidal silica | 1.0 |

| Filler | |
|---|---|
| Ingredient | Parts by Weight |
| Radiopaque glass G | 100.0 |

The filler particles were treated with a solution of a silane primer, to have a silane content of 3.5% by weight deposited thereon after drying.

As an initial step in preparing a filling composition for use, the liquid binder and the filler were mixed together to form a paste, in the ratio of 4.4 parts of filler to 1.0 parts of liquid resin binder, by weight.

The catalyst paste was made up from the following components:

| Catalyst Paste | |
|---|---|
| Ingredient | Parts by Weight |
| (methacryloylethyl)(methacryloyl-2-hydroxypropyl) hexahydro phthalate | 100.0 |
| BHT (inhibitor) | 0.12 |
| UV-9 (UV absorber) | 0.60 |
| Aerosil fumed colloidal silica | 1.0 |

| Filler | |
|---|---|
| Ingredient | Parts by Weight |
| Radiopaque glass G | 100.0 |

The glass particles were treated with silane keying agent to have silane content of 3.5% by weight, and were admixed with 0.42 parts by weight of benzoyl peroxide as a catalyst.

The resin binder and filler were mixed to form a paste, in the ratio of 4.4 parts of filler to 1.0 parts of binder, by weight.

Direct Dental Filling Composition

The two pastes were mixed in equal parts, to form a filling composition ready for use in a previously prepared cavity. The compressive strength, measured after 24 hours, was 39,048 psi, which is an acceptable value. The $C_{70}$ value was 0.52. The $C_{70}$ value is considered to be an improvement over existing formulae, and the composition had greatly improved X-ray opacity as compared to existing commercial products.

EXAMPLE 3

Use of Different Liquid Resin Binder, With 100% Radiopaque Filler

The neutral paste was prepared in the same manner as the neutral paste of Example 2. The catalyst paste was made up as follows:

| Catalyst Paste Liquid Resin Binder | |
|---|---|
| Ingredient | Parts by Weight |
| Bis/GMA | 60.0 |
| EBA | 20.0 |
| Triethylene glycol dimethacrylate | 20.0 |
| BHT (inhibitor) | 0.06 |
| UV-9 (UV absorber) | 1.5 |
| Aerosil fumed colloidal silica | 1.0 |
| Filler | |
| Ingredient | Parts by Weight |
| Radiopaque glass G | 100.0 |

The filler particles were treated with a silane keying agent solution to have a silane content of 3.5% by weight, and were admixed with 0.42 parts by weight of benzoyl peroxide as a catalyst.

The resin binder and filler were mixed to form the catalyst paste, in the ratio of 4.4 parts of filler to 1.0 parts of binder, by weight.

Direct Dental Filling Composition

The two pastes were mixed in equal parts, to form a direct dental filling composition ready to use in a previously prepared cavity. The filling composition, after curing, was evaluated as acceptable, but had an advantage over existing formulae with respect to improved X-ray opacity.

GENERAL COMMENTS

The direct dental filling compositions described in the foregoing Examples exhibited excellent initial and long-term marginal adaptation. They were well suited for filling Class I, III, IV and V cavities. Each of these compositions set in about 2 minutes after mixing. Each could be finished and polished within about 5 minutes, and each finished to a very smooth surface. Each exhibited low shrinkage and was insoluble, and thus resisted darkening at the edges and washing out.

The compositions of the three examples above are flowable pastes, for easier mixing and placing in the cavity. The following examples describe direct dental filling compositions that are also prepared by mixing two paste parts, that are placed in a prepared cavity with a spatula or syringe, but that can be carved to a desired shape. The characteristic of carvability is the result of the use of a resin binder system that cures in a first step to a semi-hard solid, like a cake of soap. In the second, subsequent cure step, the composition sets up to a Rockwell H hardness generally in the range from about 118 to about 120, compared to the value for good amalgam of about 108. Compressive strength generally is in the range from about 45,000 to 50,000 psi, well into the amalgam range. Fillings produced from these compositions have exceptional wear resistance.

With these formulations, mixing the pastes and applying the composition to a cavity is generally accomplished within about two minutes. Any flash or other excess is then trimmed off. During the period from about three minutes to about six minutes after initial mixing, the compositions can be carved. Beginning about six minutes after initial mixing, finishing can be accomplished with stones, discs, or wheels.

More specifically, the compositions described in the following examples utilize a polymerizable binder that has at least two different types of reactive groups. In these compositions, the filler constitutes from about 50% to about 80% by weight of the composition. Upon curing, these compositions reach a Shore D hardness of 85 no sooner than about two minutes after reaching a Shore D hardness of 45, at 37° C. Ordinarily, the Shore D hardness of 45 should be reached in a time not shorter than 90 seconds, but preferably in a shorter time than 120 seconds. A filling material that has a Shore D hardness of 45 is carvable. Once a Shore D hardness of 85 is attained, the material is no longer carvable. At that point it has attained roughly 30% of its ultimate, fully cured strength.

EXAMPLE 4

Carvable Direct Dental Filling Composition

This composition was made up in the form of two pastes. The neutral paste was made up from the following components:

| Neutral Paste Liquid Resin Binder | |
|---|---|
| Ingredient | Parts by Weight |
| Bis-GMA | 60.0 |
| Butene-1,4-dimethacrylate | 40.0 |
| BHT | 0.04 |
| UV-9 (UV absorber) | 0.5 |
| Accelerator A | 2.5 |
| Aerosil fumed colloidal silica | 1.0 |
| 2:1 hydroxyazo metal chelate dye | 0.008 |
| Filler | |
| Ingredient | Parts by Weight |
| Radiopaque glass G | 60.0 |
| Amorphous silica | 40.0 |

The filler particles were treated with a silane keying agent to have a silane content of 3.5% by weight.

As an initial step in preparing the filling composition for use, the binder and filler were mixed together to form a paste, in the ratio of 4.8 parts of filler to 1.0 parts of binder, by weight.

The catalyst paste was made up from the following components:

| Catalyst Paste Liquid Resin Binder | |
|---|---|
| Ingredient | Parts by Weight |
| 1-(2'-methacryloylethoxy)-2-(3'methacryloyl 2'- hydroxy propoxy) cyclohexane | 100.0 |
| BHT | 0.12 |
| UV-9 | 0.6 |
| Aerosil fumed colloidal silica | 1.0 |

| Filler | |
|---|---|
| Ingredient | Parts by Weight |
| Radiopaque glass G | 60.0 |
| Amorphous silica | 40.0 |

The filler particles were treated with a silane keying agent to have a silane content of 3.5% by weight, and were mixed with 0.41 parts by weight of benzoyl peroxide as a catalyst.

The resin binder and filler were mixed to form the catalyst paste, in the ratio of 4.2 parts of filler to 1.0 parts of binder, by weight.

Carvable Direct Dental Filling Composition

The two pastes were mixed in equal parts, to form a filling composition ready to apply to a previously prepared cavity. The compressive strength of the cured composition, measured after 24 hours, was 47,619 psi. The $C_{70}$ value was 0.50. The Rockwell H hardness was 116.2. Diametral tensile strength was 7,592 psi. Linear shrinkage was 0.91%.

EXAMPLE 5

Carvable Direct Dental Filling Composition with 100% Radiopaque Filler

A carvable direct dental filling composition was again made up in the form of two pastes, as in the previous example.

Neutral Paste

Liquid Resin Binder

The neutral paste liquid resin binder was prepared in the same manner as the binder for the neutral paste of Example 4.

| Filler | |
|---|---|
| Ingredient | Parts by Weight |
| Radiopague glass G | 100.0 grams |

The filler particles were treated with a silane keying agent to have a silane content of 3.5% by weight. The liquid resin binder and filler were mixed to form the catalyst paste, in the ratio of 4.5 parts of filler to 1.0 parts of binder, by weight.

The catalyst paste was made up from the following components:

Catalyst Paste

Liquid Resin Binder

The liquid resin binder was prepared in the same manner as the binder for the catalyst paste of Example 4.

| Filler | |
|---|---|
| Ingredient | Parts by Weight |
| Radiopaque glass G | 100.0 |

The filler particles were treated with a silane keying agent to have a silane content of 3.5% by weight, and were admixed with 0.42 parts by weight of benzoyl proxide as a catalyst. The resin binder and filler were mixed to form the catalyst paste, in the ratio of 4.4 parts of filler to 1.0 parts of binder, by weight.

Carvable Direct Dental Filling Composition

The two pastes were mixed in equal amounts, to form a filling composition ready to be applied to a previously prepared cavity. After curing, the compressive strength, measured after 24 hours, was 38,201 psi. The $C_{70}$ value was 0.47. As compared to existing formulae, X-ray opacity was greatly improved.

CONCLUDING REMARKS

The foregoing examples of carvable compositions and of single step curing compositions utilized a particular barium glass, which is a commercially available product of Corning Glass Works. Equally satisfactory results have been attained when barium glass products of Owens-Illinois, Inc. and its Kimble division have been employed in accordance with the present invention. Generally, the preferred barium glass composition is about 32% barium oxide, about 50% silicon dioxide, about 9% boron oxide, and about 9% aluminum oxide, but many other barium glasses are useful. Generally the barium oxide-based boron-alumina-silicate glasses are preferred.

The resin binders described in the examples and elsewhere in this application facilitate the production of compositions with clearly superior properties despite the content of barium glass in the filler, which is higher than anything considered feasible by the prior art. In particular, the liquid resin binders disclosed facilitate matching the refractive index of the liquid resin binder and the filler materials.

While the invention has been described in connection with specific embodiments thereof, it will be understood that it is capable of further modifications, and this application is intended to cover any variations, used, or adaptations of the invention following, in general, the principles of the invention and including such departures from the present disclosure as come within known or customary practice in the art to which the invention pertains, and as may be applied to the essential features hereinbefore set forth, and as fall within the scope of the appended claims.

What is claimed is:

1. A dental restorative composition having a filler and a liquid resin binder, that is substantially opaque to dental diagnostic X-rays, and that is formed from ingredients that facilitate matching the infractive index of the binder with that of the filler, consisting essentially of:
   from 70% to 85% by weight of the composition of a mixture of finely divided inorganic filler materials;
   from 15% to 30% by weight of the composition of a liquid resin dimethacrylate binder; and
   a curing system for the liquid resin binder that will cause curing of the composition, upon admixture of the ingredients, in less than about ten minutes;

said filler mixture consisting essentially of a transparent barium glass admixed with a different inorganic particulate filler material, that comprises amorphous silica, the barium glass providing about 60% by weight of the mixture and the balance of the mixture being an amount of a different, inorganic particulate filler material;

said barium glass being formed from a mixture of BaO, $B_2O_3Al_2O_3$, and $SiO_2$, said glass being essentially free of monovalent elements and having a BaO content of at least 22.5% by weight thereof and that is substantially equal in molar percentage to the sum of the molar percentages of $Al_2O_3$ and $B_2O_3$ respectively;

the filler content of the composition, and the BaO content of the filler, being such that the BaO content of the composition is in the range from about 15% to about 28% by weight of the composition.

2. A dental restorative composition in accordance with claim 1 wherein the liquid resin binder is formed from a mixture of dimethacrylates that includes at least 10% by weight of the liquid binder of a diluent cross-linker, and wherein said different inorganic particulate filler material is amorphous silica and constitutes about 40% of the filler mixture by weight.

3. A dental restorative composition in accordance with claim 2 wherein the mixture of dimethacrylates includes at least 30% by weight of the binder of the dimethacrylate of the diglycidyl ether of bisphenol-A and at least 10% by weight of a diluent cross-linker.

4. A dental restorative composition in accordance with claim 2 wherein at least a substantial portion of the liquid resin binder is a diester adduct of an alicyclic dicarboxylic acid selected from the group consisting of hexahydrophthalic acid, tetrahydrophthalic acid, and a maleic acid adduct of methyl cyclopentadiene.

* * * * *

UNITED STATES PATENT AND TRADEMARK OFFICE
CERTIFICATE OF CORRECTION

PATENT NO. : 4,220,582
DATED : September 2, 1980
INVENTOR(S) : Jan A. Orlowski et al.

It is certified that error appears in the above—identified patent and that said Letters Patent is hereby corrected as shown below:

Column 15, at line 9, there should be a comma and space between "$B_2O_3$" and "$Al_2O_3$".

Signed and Sealed this

Second Day of December 1980

[SEAL]

Attest:

SIDNEY A. DIAMOND

Attesting Officer

Commissioner of Patents and Trademarks

UNITED STATES PATENT OFFICE
CERTIFICATE OF CORRECTION

Patent No. 4,220,582  Dated September 2, 1980

Inventor(s) Jan A. Orlowski, Patrick D. Kidd, & David V. Butler

It is certified that error appears in the above-identified patent and that said Letters Patent are hereby corrected as shown below:

In column 14, at line 60, the word "infractive" should be -- refractive --.

*Signed and Sealed this*

*Twenty-fourth* Day of *February 1981*

[SEAL]

*Attest:*

RENE D. TEGTMEYER

*Attesting Officer*  *Acting Commissioner of Patents and Trademarks*